United States Patent
Fukuda et al.

(10) Patent No.: US 6,393,317 B1
(45) Date of Patent: May 21, 2002

(54) LIVING BODY IMPEDANCE MEASURING INSTRUMENT AND BODY COMPOSITION MEASURING INSTRUMENT

(75) Inventors: Yoshinori Fukuda, Tokyo (JP); Steven B. Heymsfield, Mount Kisco, NY (US)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/367,349

(22) PCT Filed: Feb. 24, 1998

(86) PCT No.: PCT/JP98/00736

§ 371 Date: Dec. 7, 1999

§ 102(e) Date: Dec. 7, 1999

(87) PCT Pub. No.: WO98/36686

PCT Pub. Date: Aug. 27, 1998

(30) Foreign Application Priority Data

Feb. 24, 1997 (JP) .............................................. 9-054244

(51) Int. Cl.$^7$ ................................................. A61B 5/05
(52) U.S. Cl. ........................ 600/547; 600/372; 600/382; 600/384
(58) Field of Search ................................ 600/547, 372, 600/548, 382, 384, 386, 461, 476, 477, 478; 345/174

(56) References Cited

U.S. PATENT DOCUMENTS

| | | | |
|---|---|---|---|
| 4,008,712 A | | 2/1977 | Nyboer |
| 4,949,727 A | * | 8/1990 | Yamazaki et al. .......... 128/734 |
| 5,579,782 A | * | 12/1996 | Masuo ....................... 128/734 |
| 5,746,214 A | * | 5/1998 | Brown et al. ............... 128/693 |
| 5,817,031 A | * | 10/1998 | Masuo et al. ................ 600/547 |
| 5,824,029 A | * | 10/1998 | Weijand et al. ............. 607/122 |
| 6,044,294 A | * | 3/2000 | Mortazavi et al. .......... 600/547 |
| 6,058,325 A | * | 5/2000 | Baura ............................ 607/8 |

FOREIGN PATENT DOCUMENTS

| | | |
|---|---|---|
| JP | 50-12528 | 10/1975 |
| JP | 3-27050 | 3/1991 |
| JP | 5-49050 | 7/1993 |
| JP | 7-12635 | 1/1995 |
| JP | 7-79938 | 3/1995 |
| JP | 8-154910 | 6/1996 |

OTHER PUBLICATIONS

"Assessment of Fat–Free Mass Using Bioelectrical Impedance Measurements of the Human Body", by H. Lukaski, PhD, et al., The American Journal of Clinical Nutrition, Apr. 1985, pp. 810–817.

"Body Composition Analyzer: InBody 2.0", Biospace Co., Ltd.

* cited by examiner

Primary Examiner—Marvin Lateef
Assistant Examiner—Jeoyuh Lin
(74) Attorney, Agent, or Firm—McDermott, Will & Emery (57) ABSTRACT

High frequency current application electrodes are brought into contact with both hands, both feet, etc., which are extreme parts of a body in order to apply current to the parts of the body to be measured. Potential difference measuring electrodes are brought into contact with the parts to be measured along the path of the high frequency current. High frequency current application electrodes and potential difference measuring electrodes are selected to select the path of the high frequency current and the path of the potential difference measurement in accordance with the purpose. Impedance on each of the parts of the body is measured and body composition is derived.

10 Claims, 8 Drawing Sheets

LIVING BODY IMPEDANCE MEASURING INSTRUMENT AND BODY COMPOSITION MEASURING INSTRUMENT

BACKGROUND OF THE INVENTION

1. Field of the Invention

The present invention relates to a living body impedance measuring instrument, and a body composition measuring instrument for producing a body composition in a whole body or in a part of a body of a person to be tested, based upon the living body impedance measured.

2. Description of the Prior Art

It is well known to predict a body composition using a living body impedance (see, for example, "Assessment of fat-free mass using bio-electrical impedance measurement of the human body", The American Journal of Clinical Nutrition, 41(4), 810–817, 1985). A number of body fat measuring instruments based on this principle have been proposed (see, for example, U.S. Pat. No. 4,008,721; Japanese Patent Publication No. 5-49050; and Japanese Utility Model Laid-Open No. 3-27050) and a number of "BIM" type body fat measuring instruments are now available in the market.

Those prior art instruments include two high frequency current application electrodes and two potential difference measurement electrodes required for measuring the living body impedance. One high frequency current application electrode is paired with one potential difference measurement electrode, and a high frequency current application terminal and a potential difference measurement terminal are disposed at the same end. Then they are attached to hands or feet of a human body. In order to produce a body composition, impedance values measured between a hand and a foot, between both feet or between both hands are basically utilized to derive a whole body composition. Therefore, in the past, the body composition is not necessarily produced by taking into account of a living impedance data in whole body.

If it is necessary to change the parts to be measured for getting more precision in measurement, it is frequently difficult to remove and re-attach the electrodes because of paired connection of the high frequency current application electrodes and the potential difference measuring electrodes. Sometimes, it is even necessary to take off one's clothes depending on the parts to be measured.

The prior art four-electrode measuring process can only measure the living body impedance between both feet or between both hands. Accordingly, it is difficult to measure the living body impedance a part by a part of the body.

Therefore, in case where the living body impedance should be measured a part by a part of the body, it is necessary for a skilled person to attach four or more electrodes to the relevant parts of the body. In addition, the voltage value measured should be converted into the data such as the impedance on the parts or the body compositions by using highly complicated calculation process. This involves highly expert knowledge and complicated arithmetic operations.

Another approach has been attempted using four pairs of electrodes each mounted for each of both hands and both feet. The electrodes are switched to perform measurement between different parts of the body. For example, the measurement may be performed between both hands, both feet, the right hand and the right foot, the right hand and the left foot, the left hand and the left foot or the left hand and the right foot (see Japanese Patent Laid-Open No. 9-285455).

However, such approach is defective in that the data required for calculating the values on the parts to be measured involves many unnecessary components so that the measuring process is highly complicated. In addition, even when it is desired to only measure the main body portion, it is very cumbersome to perform because of four different types of data and the different calculations based on such data required. Furthermore, because of possibility of relatively large error inherently generated in the measurement of living body impedance, an amount of error cumulatively increases in proportion to the number of different data types used. Therefore, such approach involves a higher risk especially when it is used to measure the lower impedance portions such as the main body portion.

In view of the above, there is a need to mitigate or to eliminate the disadvantages of the prior art devices as above. Therefore, one object of the present invention is to provides an improved measuring system that requires no cumbersome repeated attaching and detaching operations for the electrodes, that permits easy measurement of the impedance on each of different parts of a body, and that can produce precise values of body compositions based on the impedance data measured.

SUMMARY OF THE INVENTION

According to the present invention, high frequency current application electrodes are brought into contact with both hands, both feet, etc., which are extreme parts of a body in order to apply current to the parts of the body to be measured. Potential difference measurement electrodes are brought into contact with the parts to be measured along the path of the high frequency current. High frequency current application electrodes and potential difference measurement electrodes are selected to select the path of the high frequency current and the path of the potential difference measurement in accordance with the purpose.

Potential difference is allowed to be appeared only on the parts of a body that are included in the path of high frequency current according to 4-terminal law, and therefore, potential difference in any of sections along the path of high frequency current can be measured. As the result, the path of high frequency current and the potential difference measuring sections along the path can be selected in any combination to measure the impedance on desired parts of the body.

DESCRIPTION OF THE PREFERRED EMBODIMENTS

Figure 1:
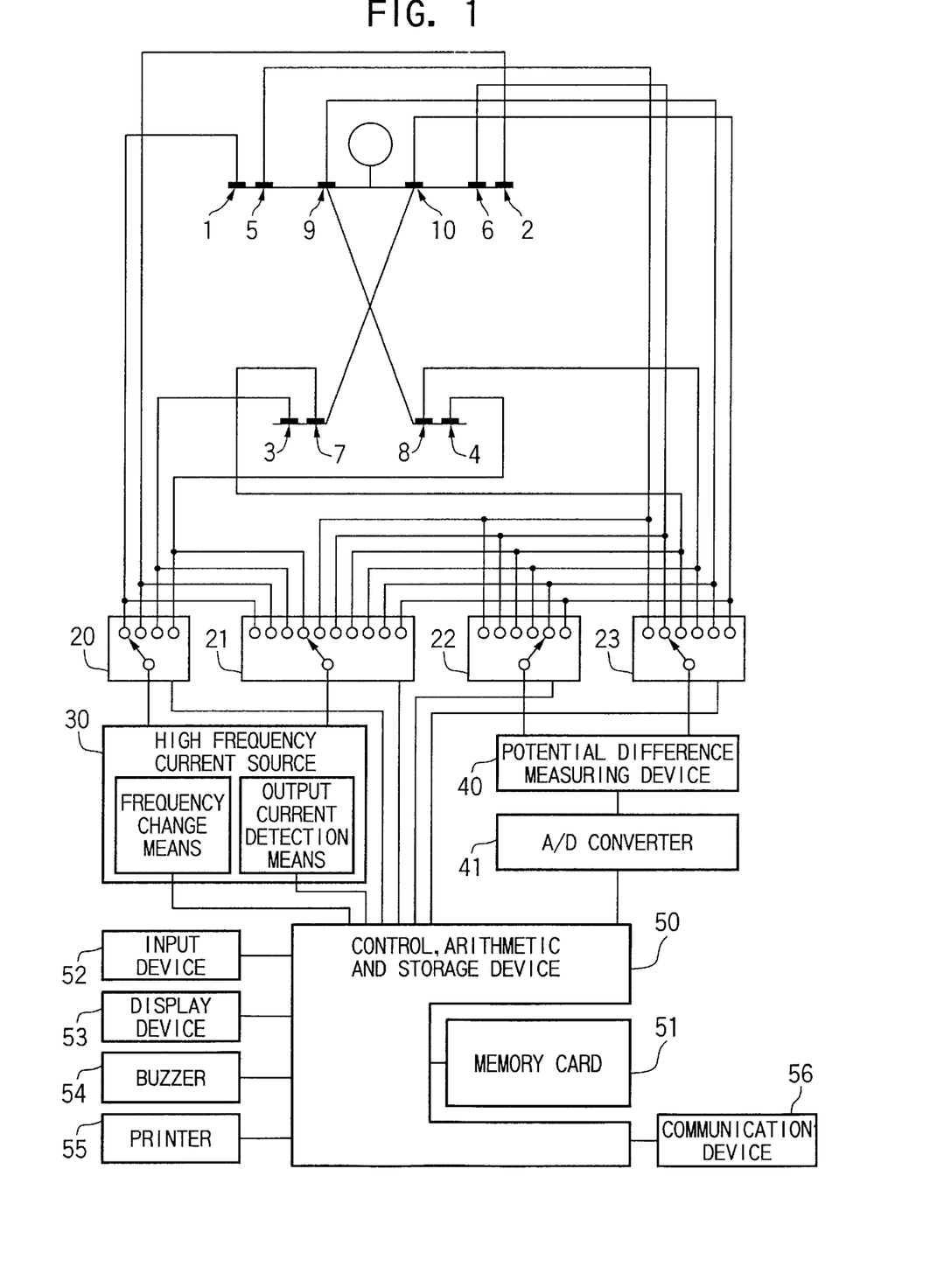
FIG. 1 is a block diagram of a system comprising a living body impedance measuring instrument and a body composition measuring instrument according to one embodiment of the present invention.

Referring now to FIG. 1, one embodiment of the present invention is shown in a block diagram. A body composition measuring instrument as shown in the figure comprises total ten electrodes. More particularly one high frequency current application electrode and one potential difference measurement electrode are mounted on each of both hands and both feet which are extreme parts of a body. In addition, one potential difference measurement electrode is mounted on each of the roots of both arms.

In the figure, reference numerals 1, 2, 3 and 4 represent the high frequency current application electrodes for applying high frequency current to the body. Those electrodes 1, 2, 3 and 4 are connected to switching means 20 and 21 which are then connected to output terminals of a high frequency current source 30. Electrodes 5, 6, 7, 8, 9 and 10 are connected to switching means 21, 22 and 23. The switching means 22 and 23 are connected to a potential difference measuring device 40, and the switching means 21 is connected to output terminals of the high frequency current source 30. The electrodes 5, 6, 7, 8, 9 and 10 are used for measurement of potential difference, but they may also act as the high frequency current application electrodes for applying high frequency current to the body.

The switching means 20, 21, 22 and 23 are connected to a control, arithmetic and storage device 50 so that they can independently operate to switch the electrodes according to control signals from the device 50.

The high frequency current source 30 connected to the switching means 20 and 21 comprises a current detection means for detecting its output current and a frequency change means for changing the frequency of high frequency current, both means are connected to the control, arithmetic and storage device 50. The current detection means functions to inform the detection result to the arithmetic and storage device 50, and the frequency change means functions to change the frequency of high frequency current according to the control signals from the control, arithmetic and storage device 50.

The switching means 22 and 23 are connected to the potential difference measuring device 40 whose output is connected to the control, arithmetic and storage device 50 via an A/D converter 41. The A/D converter 41 functions to convert the output of the potential difference measuring device 40 into digital values which are then fed to the control, arithmetic and storage device 50.

An input device 52 is connected to the control, arithmetic and storage device 50 for entering some instructions for operations of the system and parameters for a person to be tested such as height and weight of the person.

A display device 53 connected to the control, arithmetic and storage device 50 functions to display parameter settings for the person to be tested, measurement results, and some indications indicating when an error occurs. A buzzer 54 is activated to generate a tone at the time when the measurement is started, the measurement is completed, and any error occurs. A printer 55 produces a hard copy of the measurement results.

A communication device 56 is connected to the control, arithmetic and storage device 50 in order to communicate between the system and the external devices. The communication device 56 functions to transmit the measurement results to the external devices, while it receives the parameters for the person to be tested and the instructions for operation of the system from the external devices.

In the embodiment as shown, a memory card is used for the removable storage medium. The parameters used for the measurement and the data such as the measurement results are stored in the memory card through the control, arithmetic and storage device 50.

The control, arithmetic and storage device 50 functions to selectively activate the switching means 20, 21, 22 and 23 and to control changing of the frequency of the high frequency current. In addition, the device 50 functions to perform an arithmetic operation, based on the data or parameters for the person to be tested (which are entered from the input device, the communication device and the memory card), as well as on the data obtained by the measurement. As the result, the device 50 produces the values of impedance and the body composition, which are then fed to the output devices, the communication device and the memory card.

Figure 10:
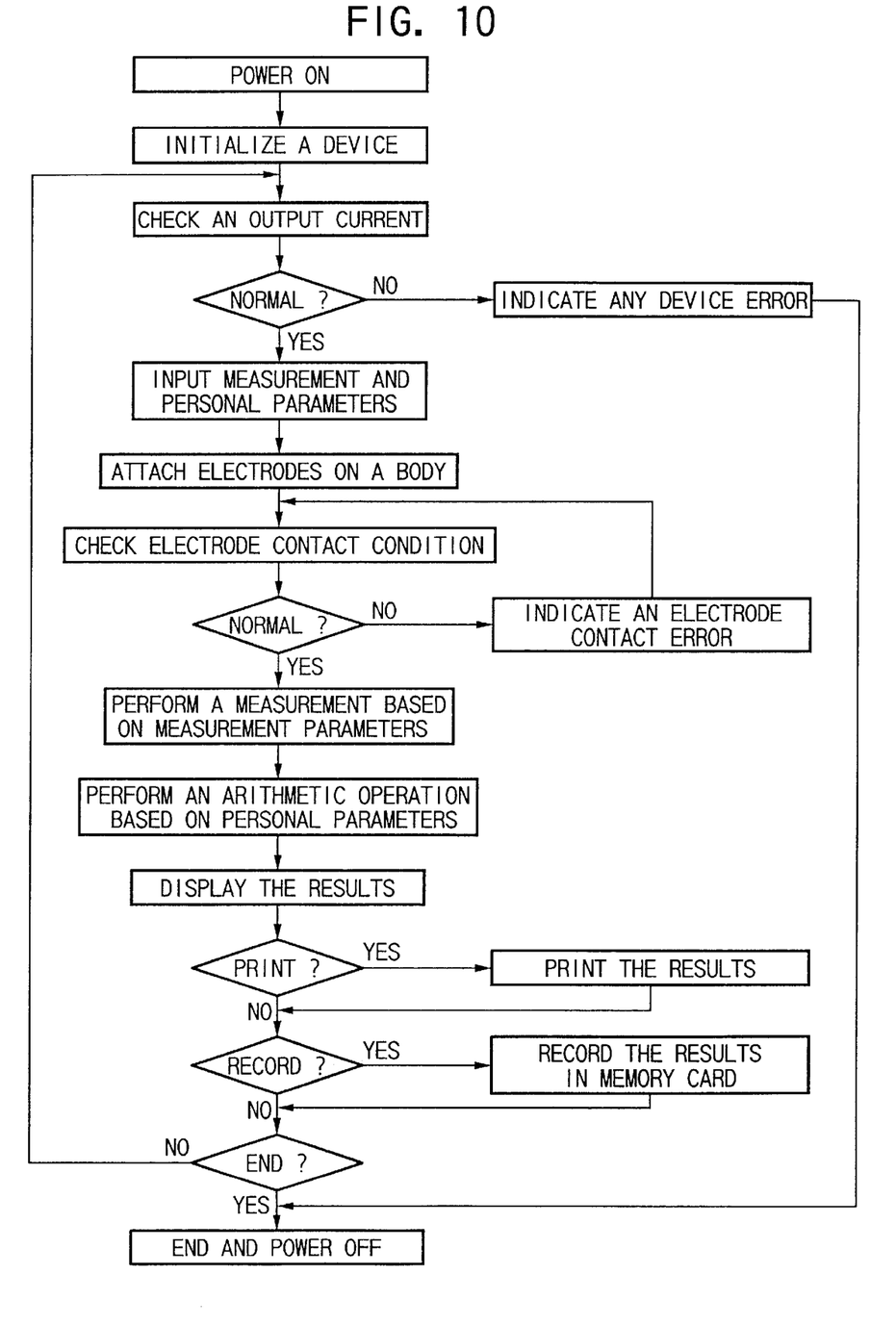
FIG. 10 is a flow chart showing the operations of the system according to the present invention.

A sequence of measuring steps and details of measurement in this embodiment will be described below (with reference to FIG. 10 that shows the flow of the measurement steps). In this embodiment, in order to prevent excessive current from passing through the body due to any defect of the device, before attaching the electrodes to the body, the same electrode is selected by the switching means 20 and 21. This is for the purpose of self-diagnosis for finding out whether the output current is at normal level or at abnormal level. If it is found that the output current is at abnormal level, the measurement is stopped with an indication on the display device that indicates some abnormal condition prevailing in the system.

If the self-diagnosis is successfully done, the parameters for the person to be tested and the instructions for operations of the system are entered by the input device 52. Then, the electrodes are attached to both hands, both feet and the roots of both arms.

Before starting the measurement process, in order to examine the contact condition of each electrode, any two different electrodes are selected by the switching means 20 and 21, and the check is made to see if the current passing therebetween is at normal level or not. If an abnormal current passes, it means that any one of or both of the electrodes selected is in poor contact or no contact condition.

More particularly, while the electrode 1 is kept selected by the switching means 20, one of the electrodes 2 to 10 is sequentially selected by the switching means 21 for examination. If it is found that an abnormal current passes when the electrodes 5 and 10 are selected, it means that the electrodes 5 and 10 are in poor contact or no contact condition. It may happen that all the electrodes 2 to 10 are found abnormal after they are sequentially selected by the switching means 21. In such case, the electrodes 2 is kept selected by the switching means 20 and any one of the electrodes 3 to 10 is sequentially selected by the switching means 21. In such manner, any poor contact or no contact condition of the electrodes can be detected.

Because of all the electrodes arranged to apply current to the body, the examination of the electrode contact condition can be performed depending on whether the current passing to the body from the high frequency current source is at normal level, or within the normal range, or at abnormal level. This greatly reduces the time period required for the examination. In view of such examination made before starting the measurement, it is unlikely that the measurement process would inevitably be interrupted in the course of measurement due to any defective contact of the electrodes.

If any abnormal is found out in the examination of electrode contact condition, the buzzer device may sound and/or the display device may display which electrode (or electrodes) is in poor contact or no contact condition, or which electrode is becoming to such condition.

If no abnormal is found in the examination of electrode contact condition, then the measurement is started.

Figure 2:
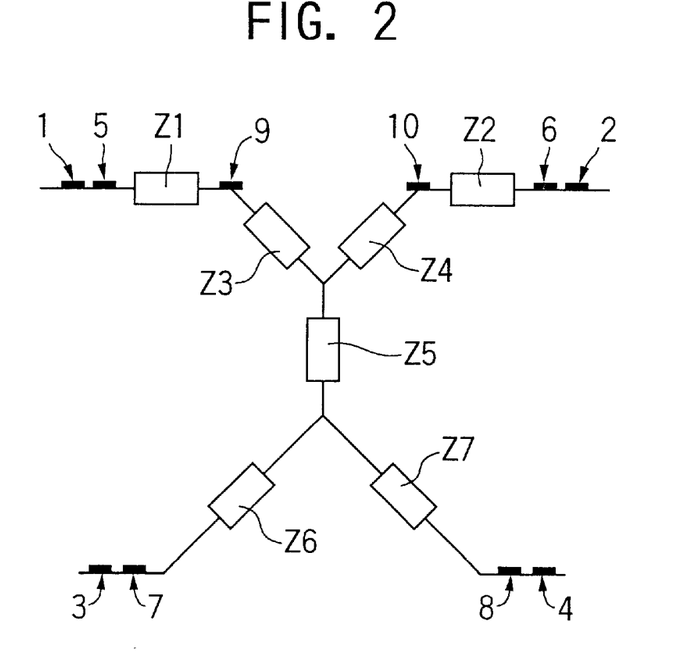
FIG. 2 is an equivalent circuit diagram of the living body impedance measuring instrument and the body composition measuring instrument according to one embodiment of the present invention.

For the purpose of describing the-present invention, some terms used herein are defined. Referring to FIG. 2 that is the equivalent circuit diagram of the human body, "Z1" and "Z2" mean the impedance of arms; "Z3" and "Z4" mean the impedance of the chest portion; "Z5" means the impedance of the abdominal region; and "Z6" and "Z7" mean the impedance of legs. The electrodes 1 and 5 are attached to and brought into contact with the right hand. Similarly, the electrodes 2 and 6 are attached to the left hand. The electrodes 3 and 7 are attached to the right foot. The electrodes 4 and 8 are attached to the left foot. Finally, the electrode 9 is attached to the root of the right arm, and the electrode 10 is attached to the root of the left arm. Then, the impedance "Z1" is called a "right arm impedance"; "Z2" a "left arm impedance"; "Z3" a "right chest impedance"; "Z4" a "left chest impedance"; "Z5" a "abdominal impedance"; "Z6" a "right leg impedance"; and "Z7" a "left leg impedance".

The seven impedance "Z1" to "Z7" as indicated in the equivalent circuit of a human body are then measured according to the present invention, as described below.

Figure 3:
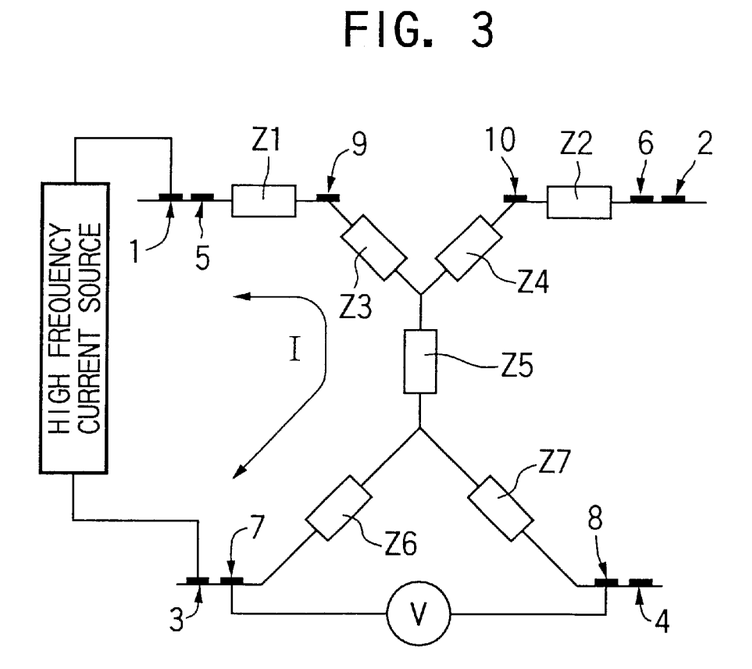
FIG. 3 is an equivalent circuit diagram of the living body impedance measuring instrument and the body composition measuring instrument when they are arranged to measure the impedance on both legs of a person.

When measuring the right leg impedance Z6, the electrode 1 is selected by the switching means 20, the electrode 3 is selected by the switching means 21, the electrode 8 is selected by the switching means 22, and the electrode 7 is selected by the switching means 23. Then, as shown in FIG. 3, the high frequency current I flows through the impedance Z1, Z3, Z5 and Z6 between the electrodes 1 and 3, but it does not flow through the impedance Z7. Therefore, potential difference as measured between the electrodes 7 and 8 is represented by the following formula:

Potential Difference $V=Z6 \cdot I$

Then, the right leg impedance Z6 can be derived.

Similarly, when measuring the left leg impedance Z7, the electrode 2 is selected by the switching means 20, the electrode 4 is selected by the switching means 21, the electrode 7 is selected by the switching means 22, and the electrode 8 is selected by the switching means 23. Then, the high frequency current I flows through the impedance Z2, Z4, Z5 and Z7 between the electrodes 2 and 4, but it does not flow through the impedance Z1. Therefore, potential difference as measured between the electrodes 7 and 8 is represented by the following formula:

Potential Difference $V=Z7 \cdot I$

Then, the left leg impedance Z7 can be derived.

Figure 4:
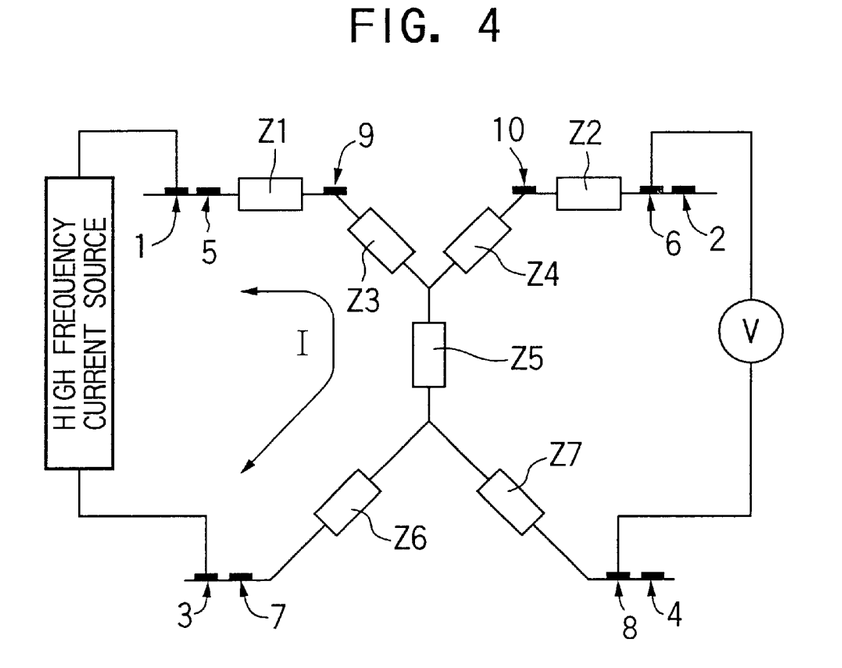
FIG. 4 is an equivalent circuit diagram of the living body impedance measuring instrument and the body composition measuring instrument when they are arranged to measure the impedance on an abdominal region of a person.

When measuring the abdominal impedance Z5, the electrode 1 is selected by the switching means 20, the electrode 3 is selected by the switching means 21, the electrode 6 is selected by the switching means 22, and the electrode 8 is selected by the switching means 23. Then, as shown in FIG. 4, the high frequency current I flows through the impedance Z1, Z3, Z5 and Z6 between the electrodes 1 and 3, but it does not flow through the impedance Z2, Z4 and Z7. Therefore, potential difference as measured between the electrodes 6 and 8 is represented by the following formula:

Potential Difference $V=Z5 \cdot I$

Then, the abdominal impedance Z5 can be derived.

Figure 5:
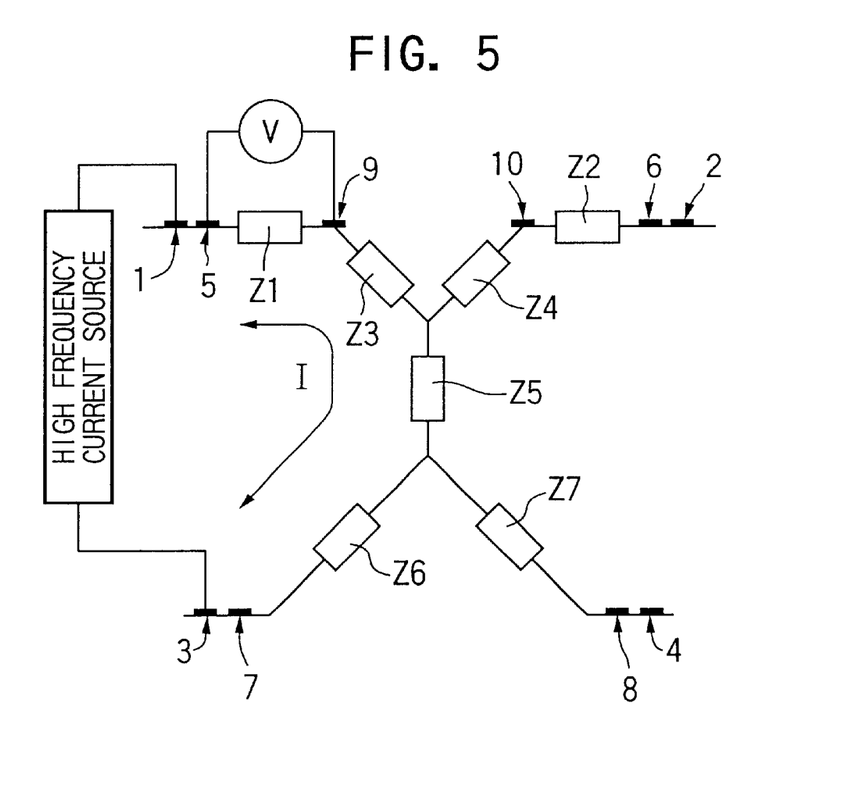
FIG. 5 is an equivalent circuit diagram of the living body impedance measuring instrument and the body composition measuring instrument when they are arranged to measure the impedance on both arms of a person.

When measuring the right arm impedance Z1, the electrode 1 is selected by the switching means 20, the electrode 3 is selected by the switching means 21, the electrode 5 is selected by the switching means 22, and the electrode 9 is selected by the switching means 23. Then, as shown in FIG. 5, the high frequency current I flows through the impedance Z1, Z3, Z5 and Z6 between the electrodes 1 and 3. Therefore, potential difference as measured between the electrodes 5 and 9 is represented by the following formula:

Potential Difference $V=Z1 \cdot I$

Then, the right arm impedance Z1 can be derived.

Similarly, when measuring the left arm impedance Z2, the electrode 2 is selected by the switching means 20, the electrode 4 is selected by the switching means 21, the electrode 6 is selected by the switching means 22, and the electrode 10 is selected by the switching means 23. Then, the high frequency current I flows through the impedance Z2, Z4, Z5 and Z7 between the electrodes 2 and 4. Therefore, potential difference as measured between the electrodes 6 and 10 is represented by the following formula:

Potential Difference $V=Z2 \cdot I$

Then, the left arm impedance Z2 can be derived.

Figure 6:
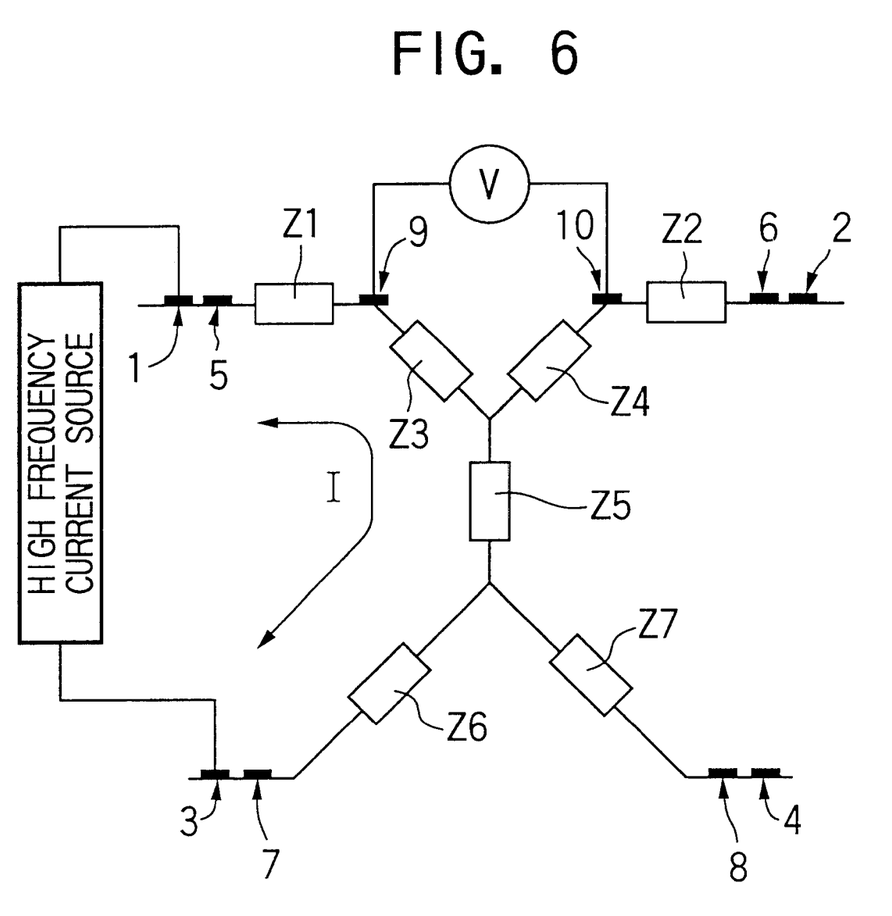
FIG. 6 is an equivalent circuit diagram of the living body impedance measuring instrument and the body composition measuring instrument when they are arranged to measure the impedance on a chest portion of a person.

When measuring the right chest impedance Z3, the electrode 1 is selected by the switching means 20, the electrode 3 is selected by the switching means 21, the electrode 9 is selected by the switching means 22, and the electrode 10 is selected by the switching means 23. Then, as shown in FIG. 6, the high frequency current I flows through the impedance Z1, Z3, Z5 and Z6 between the electrodes 1 and 3, but it does not flow through the impedance Z4. Therefore, potential difference as measured between the electrodes 9 and 10 is represented by the following formula:

Potential Difference $V=Z3 \cdot I$

Then, the right chest impedance Z3 can be derived.

Similarly, when measuring the left chest impedance Z4, the electrode 2 is selected by the switching means 20, the electrode 4 is selected by the switching means 21, the electrode 10 is selected by the switching means 22, and the electrode 9 is selected by the switching means 23. Then, the high frequency current I flows through the impedance Z2, Z4, Z5 and Z7 between the electrodes 2 and 4, but it does not flow through the impedance Z3. Therefore, potential difference as measured between the electrodes 9 and 10 is represented by the following formula:

Potential Difference $V = Z4 \cdot I$

Then, the left chest impedance Z4 can be derived.

As described above, the impedance on each of the parts of the body as shown in FIG. 2 are measured in accordance with 4-terminal law. The measurement results are transmitted to the control, arithmetic and storage device 50. On the other hand, the data such as the parameters of the person to be tested are entered and stored in the control, arithmetic and storage device 50 by using the input device in advance. The control, arithmetic and storage device 50 performs the arithmetic operations based on the measurement results and the parameter data to produce the body composition in part of or in whole of the body as well as the distribution for each of the composition components. As the result, the difference in right-to-left of the arms, chest portions and legs can be derived and they are output to the display device for indication.

In addition, the impedance measurement is performed again, but with the change in frequency of the high frequency current, and "Cole-Cole plot law" is applied to the measurement results. Then, the amount of intracellular or extracellular fluid as well as the water content in each of the parts of the body can be derived. The measurement results and the parameters of a persons to be tested can partly or wholly be output to the printer device for printing, or transmitted to the external devices via the communication device, or stored in the memory card, depending on the applications, under the control of the control, arithmetic and storage device 50.

One embodiment of the present invention has been described above. However, depending on the selection of the electrodes used for the measurement, the measurement of only living impedance between both hands, between both feet, or between a hand and a foot can, of course, be done, as in the case of the prior art.

Apart from the embodiment as above wherein all the parts of the body are measured, only some of the parts, for example, the upper half of the body including both arms and chest portions, may be measured. In such case, the difference in composition for right and left arms and chest portions can be determined from the measurement results.

Figure 8:
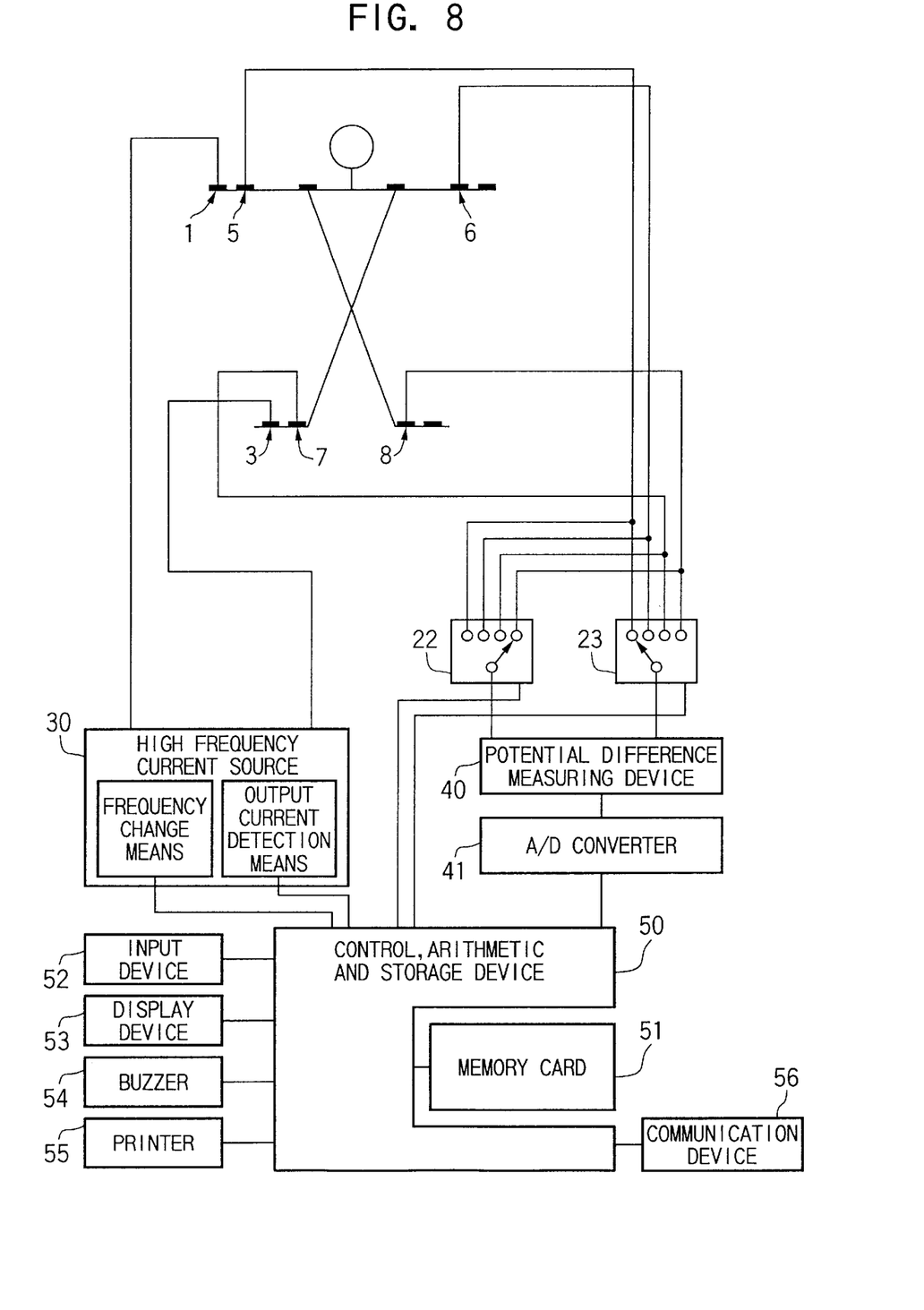
FIG. 8 is a block diagram of a system comprising a living body impedance measuring instrument and a body composition measuring instrument according to further embodiment of the present invention.

Forgoing is the description of the embodiment wherein the impedance on all the parts of the body are measured. Referring to FIG. 8, another embodiment of the present invention is shown in which two high frequency current application electrodes are each attached to the right hand and the right foot, and four potential difference measurement electrodes are each attached to both hands and both foot. According to this embodiment, each of the impedance "Z1+Z3", "Z5" and "Z6" can be determined in one measurement operation simply by changing the measurement path. Although not shown in the figure, another arrangement is possible wherein two high frequency current application electrodes are each attached to both hands, and four potential difference measurement electrodes are each attached to both hands and to the roots of both arms. In such case, the impedance "Z1" and "Z2" can be determined by changing the potential difference measurement path.

Figure 7:
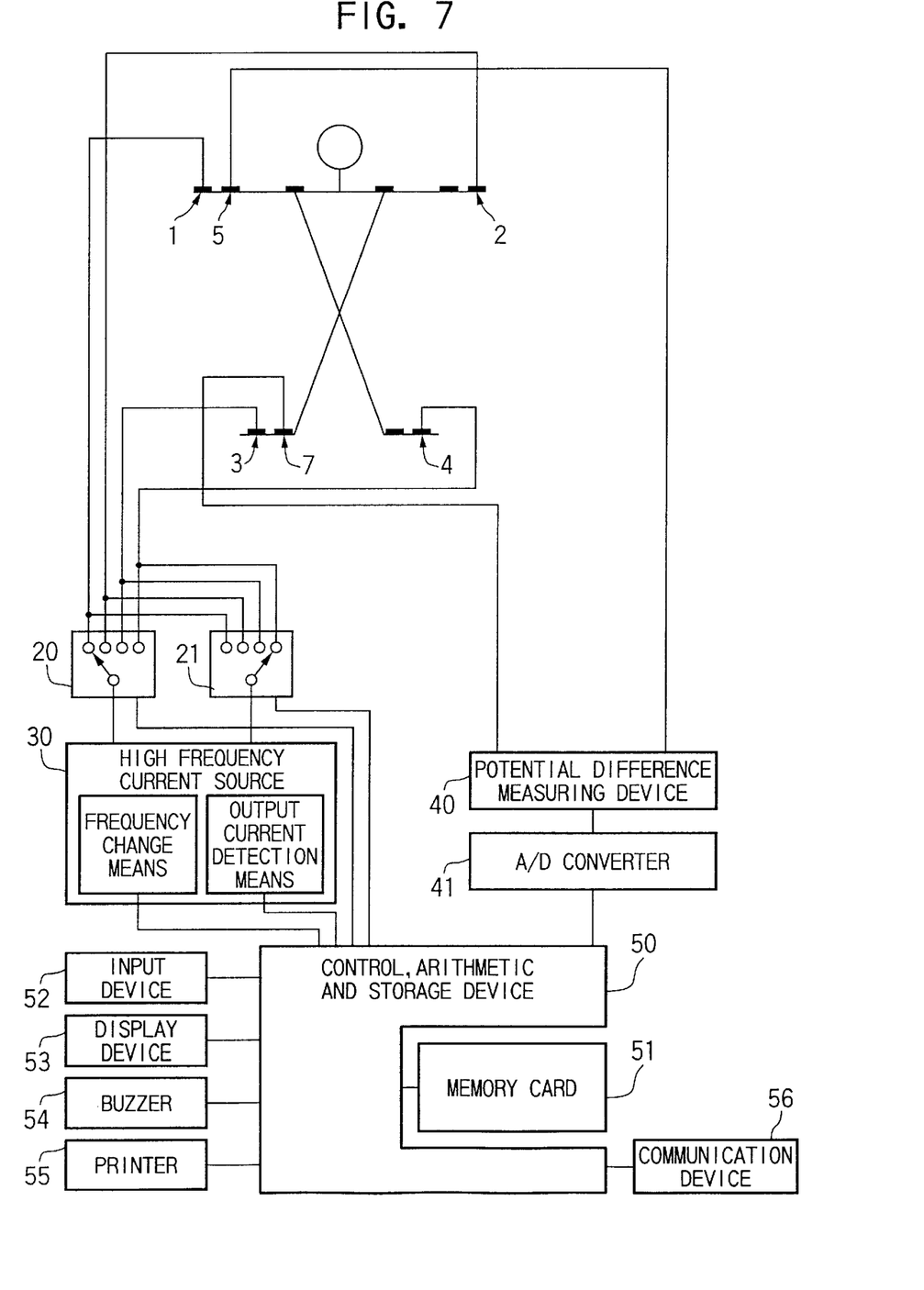
FIG. 7 is a block diagram of a system comprising a living body impedance measuring instrument and a body composition measuring instrument according to another embodiment of the present invention.
Figure 9:
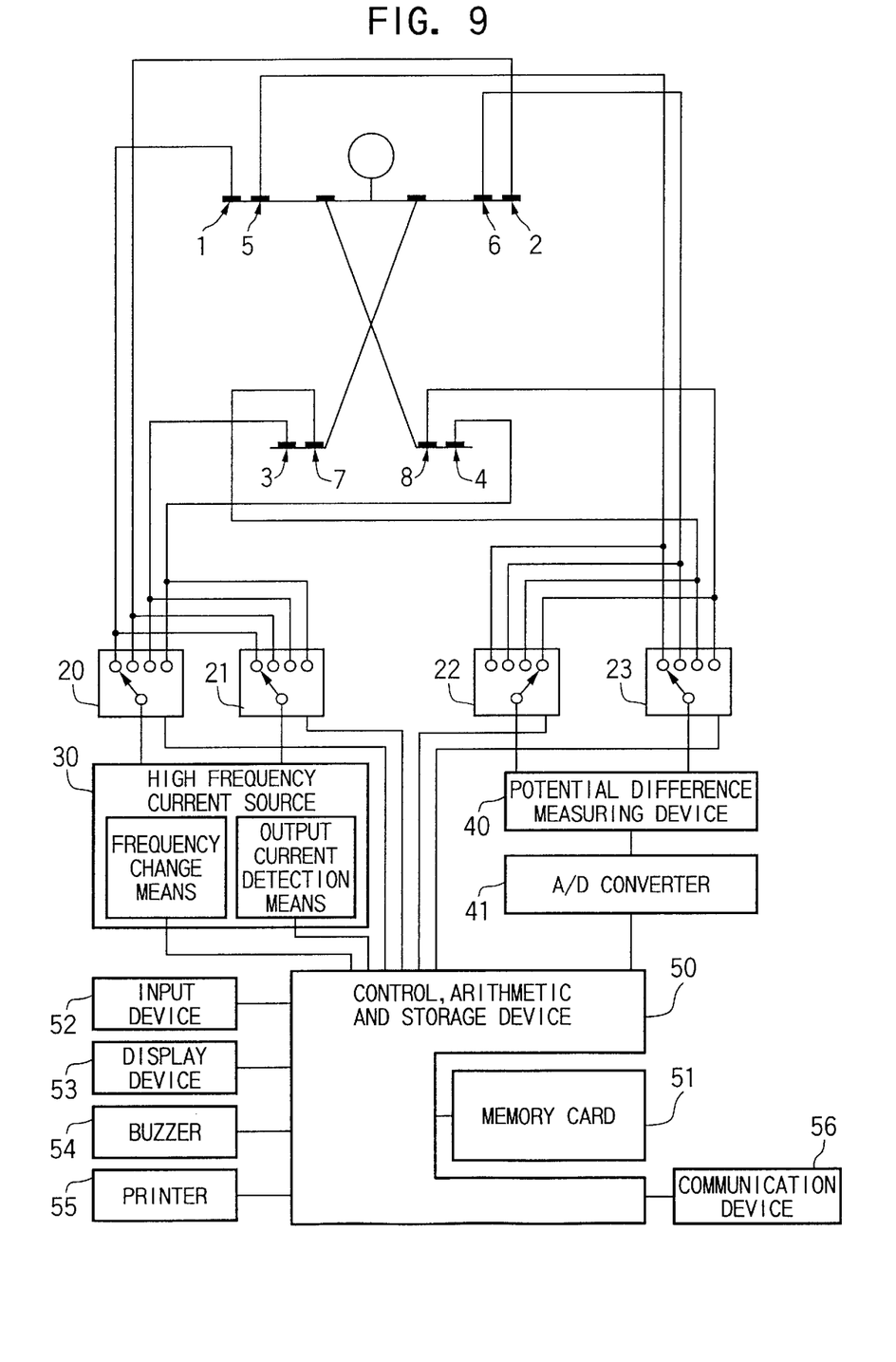
FIG. 9 is a block diagram of a system comprising a living body impedance measuring instrument and a body composition measuring instrument according to yet further embodiment of the present invention.

Referring to FIG. 7, further embodiment of the present invention is shown in which two potential difference measurement electrodes are each attached to the right hand and the right foot, and four high frequency current application electrodes are each attached to both hands and both feet. According to such embodiment, each of the impedance "Z1+Z3", "Z5" and "Z6" can be determined in one measurement operation simply by changing the current application path. Referring to FIG. 9, yet further embodiment of the present invention is shown in which a pair of the high frequency current application electrode and the potential difference measurement electrode is attached to both hands and both feet, respectively. According to such embodiment, each of the impedance "Z1+Z3", "Z2+Z4", "Z5", "Z6" and "Z7" for all the parts of the body can be determined in one measurement operation by independently changing the current application path and the potential difference measurement path.

It is apparent from the foregoing that the living impedance on each of the parts of a human body can easily be measured so that calculation and assessment of the body composition on each of the parts can be performed. Therefore, the whole body composition derived from such results is contributed by the living impedance information in whole body, thereby improving the accuracy in measurement for the whole body composition.

If it is desired that the composition on only a part of the body is known, the measurement on only that part of the body can be done. It takes shorter time period and relieves the discomfort of a person to be tested.

In case where a person was injured on one arm and was subjected to treatment for longer period of time, it is effective to use the composition on the normal arm as the criteria of decision for restoration. In such case, only the part of the body that the person wants to know can be measured within shorter period of time, which relieves the discomfort of the injured person.

Furthermore, the information indicating the parts of the body to be measured and the changing sequence of the electrodes required for the measurement may be entered to the system in advance as the measurement parameters. In such case, any specified part of the body can be measured simply by selecting any one of the parameters without any complicated operation. Such measurement and operation can easily be done by everybody or unskilled person.

What is claimed is:

1. A living body impedance measuring instrument comprising:

a high frequency current generation source for generating a high frequency current to be applied to a living body;

a plurality of high frequency current application electrodes electrically connected to the high frequency current generation source for applying the high frequency current to the living body;

a first switching device electrically connected between the high frequency current generation source and said plurality of high frequency current application electrodes for enabling application of the high frequency current along a current path between different electrodes of said plurality of high frequency current application electrodes;

a potential difference measuring device electrically connected to the high frequency current generation source for measuring a potential difference between potential difference measuring electrodes;

a plurality of potential difference measuring electrodes electrically connected to the potential difference measuring device for measuring a potential difference in the living body;

a second switching device electrically connected between the potential difference measuring device and said plurality of potential difference measuring electrodes, and electrically connected between said plurality of potential difference measuring electrodes and the first switching device, for enabling measurement of potential difference in different parts of said living body; and a control and arithmetic device electrically connected to the first and second switching devices, the high frequency current generation source, the potential difference measuring device, whereby said control and arithmetic device controls said first and second switching devices so that they are independently actuated in such a manner that the potential difference on the target part of the living body can be measured, and performs a process for converting a voltage value obtained from said potential difference measuring device into the impedance of said target part;

said plurality of high frequency current application electrodes including a plurality of electrodes each adapted to contact with each of hands or feet which are extreme parts of the living body; and said plurality of potential difference measuring electrodes including a plurality of electrodes each adapted to contact with each of hands or feet which are extreme parts of the living body and along the path of the high frequency current applied to the living body by the high frequency current application electrodes, and at least one electrode adapted to contact any one of connecting parts between the hands or feet and the trunk of the living body, for measuring the living body impedance of an arm or a leg.

2. A living body impedance measuring instrument comprising:

a high frequency current generation source for generating a high frequency current to be applied to a living body;

a plurality of high frequency current application electrodes electrically connected to the high frequency current generation source for applying the high frequency current to the living body:

a first switching device electrically connected between the high frequency current generation source and said plurality of high frequency current application electrodes for enabling application of the high frequency current along a current path between different electrodes of said plurality of high frequency current application electrodes;

a potential difference measuring device electrically connected to the high frequency current generation source for measuring a potential difference between potential difference measuring electrodes;

a plurality of potential difference measuring electrodes electrically connected to the potential difference measuring device for measuring a potential difference in the living body;

a second switching device electrically connected between the potential difference measuring device and said plurality of potential difference measuring electrodes, and electrically connected between said plurality of potential difference measuring electrodes and the first switching device, for enabling measurement of potential difference in different parts of said living body; and a control and arithmetic device electrically connected to the high frequency current generation source, the potential difference measuring device, the first switching device, and to the second switching device, whereby said control and arithmetic device controls said first and second switching devices so that they are independently actuated in such a manner that the potential difference on the target part of the living body can be measured, and performs process for converting a voltage value obtained from said potential difference measuring device into the impedance of said target part;

said plurality of high frequency current application electrodes four electrodes each adapted to contact with each of both hands and both feet are extreme parts of the living body; and said plurality of potential difference measuring electrodes including four electrodes each adapted to contact with each of both hands and feet which are extreme parts of the living body and along the path of the high frequency current applied by said high frequency current application electrodes, and two electrodes each adapted to contact with each of the roots of both arms, for measuring the living body impedance of one of the arms.

3. A living body impedance measuring instrument comprising:

a high frequency current generation source for generating a high frequency current to be applied to a living body;

a plurality of high frequency current application electrodes electrically connected to the high frequency current generation source for applying the high frequency current to the living body;

a potential difference measuring device electrically connected to the high frequency current generation source for measuring a potential difference between potential difference measuring electrodes;

a plurality of potential difference measuring electrodes connected to the potential difference measuring device for measuring a potential difference in the living body; and a control and arithmetic device electrically connected to the high frequency current generation source and to the potential difference measuring device, whereby said control and arithmetic device performs a process for converting a voltage value obtained from said potential difference measuring device into the impedance of said target part;

said plurality of high frequency current application electrodes including two electrodes each adapted to contact with each of hand and foot of the right or left side of the living body; and said plurality of potential difference measuring electrodes including one electrode adapted to contact with said hand and along the path of the high frequency current applied by said high frequency current application electrodes and one electrode adapted to contact with a root of an arm of said side of the living body, for measuring the living body impedance of the arm.

4. A living body impedance measuring instrument comprising:

a high frequency current generation source for generating a high frequency current to be applied to a living body;

a plurality of high frequency current application electrodes electrically connected to the high frequency current generation source for applying the high frequency current to the living body;

a potential difference measuring device electrically connected to the high frequency current generation source for measuring a potential difference between potential difference measuring electrodes; and a plurality of potential difference measuring electrodes electrically connected to the potential difference measuring device for measuring a potential difference in the living body;

a control and arithmetic device electrically connected to the high frequency current generation source and to the potential difference measuring device, whereby said control and arithmetic device performs a process for converting a voltage value obtained from said potential difference measuring device into the impedance of said target part;

said plurality of high frequency current application electrodes including two electrodes each adapted to contact with each of hand and foot of the right or left side of the living body; and said plurality of potential difference measuring electrodes including two electrodes each adapted to contact with each of the roots of both arms, for measuring the living body impedance of one of the arms.

5. A body composition measuring instrument in combination with a living body impedance measuring instrument according to any one of claims 1 to 4 wherein the body composition measuring instrument produces a body composition measurement for a whole body, a body composition measurement for a part of the body, or both a body composition measurement for a whole body and a body composition measurement for a part of the body, based upon the living body impedance as derived from said living body impedance measuring instrument, and from the physical characteristics of a part to be measured.

6. A living body impedance measuring instrument according to any one of claims 1 to 4 wherein the living body impedance measuring instrument comprises a removable recording medium; and wherein said control and arithmetic device instructs to store the data derived by the measurement and arithmetic operation to said recording medium.

7. A living body impedance measuring instrument according to any one of claims 1 to 4 wherein the living body impedance measuring instrument comprises a communication device for communication with the outside of the instrument; and wherein said control and arithmetic device instructs to output the data derived by the measurement and arithmetic operation via the communication device.

8. A living body impedance measuring instrument according to any one of claims 1 to 4 wherein the living body impedance measuring instrument comprises a communication device for communication with the outside of the instrument; and wherein said control and arithmetic device instructs to input the data required for the arithmetic operation via the communication device.

9. A method of making a living body impedance measuring instrument comprising the steps of:

electrically connecting a high frequency current generation source for generating a high frequency current to be applied to a living body to a plurality of high frequency current application electrodes for applying the high frequency current to the living body;

electrically connecting a first switching device between the high frequency current generation source and said plurality of high frequency current application electrodes for enabling application of the high frequency current along a current path between different electrodes of said plurality of high frequency current application electrodes;

electrically connecting a potential difference measuring device to the high frequency current generation source for measuring a potential difference between potential difference measuring electrodes;

electrically connecting a plurality of potential difference measuring electrodes to the potential difference measuring device for measuring a potential difference in the living body;

electrically connecting a second switching device between the potential difference measuring device and said plurality of potential difference measuring electrodes, and electrically connecting said second switching device between said plurality of potential difference measuring electrodes and the first switching device, for enabling measurement of potential difference in different parts of said living body; and electrically connecting a control and arithmetic device to the high frequency current generation source, the potential difference measuring device, the first switching device, and to the second switching device, whereby said control and arithmetic device controls said first and second switching devices so that they are independently actuated in such a manner that the potential difference on the target part of the living body can be measured, and performs a process for converting a voltage value obtained from said potential difference measuring device into the impedance of said target part;

said plurality of high frequency current application electrodes including four electrodes each adapted to contact with each of both hands and both feet which are extreme parts of the living body; and said plurality of potential difference measuring electrodes including four electrodes each adapted to contact with each of both hands and feet which are extreme parts of the living body and along the path of the high frequency current applied by said high frequency current application electrodes, and two electrodes each adapted to contact with each of the roots of both arms.

10. A method of making a living body impedance measuring instrument comprising the steps of:

electrically connecting a high frequency current generation source for generating a high frequency current to be applied to a living body to a plurality of high frequency current application electrodes for applying the high frequency current to the living body;

electrically connecting a potential difference measuring device to the high frequency current generation source for measuring a potential difference between potential difference measuring electrodes;

electrically connecting a plurality of potential difference measuring electrodes to the potential difference measuring device for measuring a potential difference in the living body; and electrically connecting a control and arithmetic device to the high frequency current generation source and to the potential difference measuring device, whereby said control and arithmetic device performs a process for converting a voltage value obtained from said potential difference measuring device into the impedance of said target part;

said plurality of high frequency current application electrodes including two electrodes each adapted to contact with each of hand and foot of the right or left side of the living body; and said plurality of potential difference measuring electrodes including two electrodes each adapted to contact with each of the roots of both arms.

* * * * *